(12) United States Patent
Simandan et al.

(10) Patent No.: US 9,193,742 B2
(45) Date of Patent: Nov. 24, 2015

(54) CONTINUOUS PROCESS FOR THE PREPARATION OF THIOCARBOXYLATE SILANE

(71) Applicant: Momentive Performance Materials Inc., Waterford, NY (US)

(72) Inventors: Tiberiu Ladislau Simandan, Termoli (IT); Andrea Trotto, Termoli (IT); Ilaria Vecchi, Casalbordino (IT); Ottavio Ursitti, Termoli (IT)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/326,886

(22) Filed: Jul. 9, 2014

(65) Prior Publication Data

US 2015/0080595 A1 Mar. 19, 2015

Related U.S. Application Data

(60) Provisional application No. 61/844,558, filed on Jul. 10, 2013.

(51) Int. Cl.
*C07F 7/18* (2006.01)
*B01J 31/02* (2006.01)

(52) U.S. Cl.
CPC ............ *C07F 7/1876* (2013.01); *B01J 31/0239* (2013.01); *C07F 7/1836* (2013.01); *C07F 7/1892* (2013.01)

(58) Field of Classification Search
CPC .... C07F 7/1876; C07F 7/1892; C07F 7/1836; C07C 327/06
See application file for complete search history.

(56) References Cited

U.S. PATENT DOCUMENTS

| 4,613,491 | A  | * | 9/1986  | Jung et al. ...................... 423/347 |
| 6,294,683 | B1 |   | 9/2001  | Johnson et al. |
| 6,528,673 | B2 |   | 3/2003  | Cruse et al. |
| 7,528,273 | B2 |   | 5/2009  | Simandan et al. |
| 7,781,606 | B2 |   | 8/2010  | Cruse et al. |
| 8,008,520 | B2 |   | 8/2011  | Cruse et al. |
| 8,008,524 | B2 |   | 8/2011  | Cruse et al. |
| 8,097,743 | B2 |   | 1/2012  | Glatzer et al. |
| 2003/0130388 | A1 |   | 7/2003  | Luginsland et al. |
| 2006/0235236 | A1 | * | 10/2006 | Simandan ..................... 556/429 |

FOREIGN PATENT DOCUMENTS

| JP | 2003/206274 A  | 7/2003 |
| WO | 2005/007660 A1 | 1/2005 |
| WO | 2005/007662 A2 | 1/2005 |

OTHER PUBLICATIONS

International Search Report and Written Opinion mailed Oct. 10, 2014.
U.S Appl. No. 14/228,345 current claims.

* cited by examiner

*Primary Examiner* — Sudhakar Katakam
(74) *Attorney, Agent, or Firm* — Dominick G. Vicari

(57) ABSTRACT

The invention is directed to a process for the preparation of thiocarboxylate silane comprising reacting an aqueous solution of a salt of a thiocarboxylic acid with a haloalkylalkoxysilane in the presence of a solid supported catalyst. The invention is also directed to a process for the preparation of an aqueous solution of a salt of a thiocarboxylic acid which comprises reacting an aqueous solution of a sulfide and/or hydrosulfide with a carboxylic acid halide and/or acid anhydride.

30 Claims, 4 Drawing Sheets

US 9,193,742 B2

CONTINUOUS PROCESS FOR THE PREPARATION OF THIOCARBOXYLATE SILANE

This utility patent application claims priority to U.S. Provisional Patent Application No. 61/844,558, dated Jul. 10, 2013, the entire contents of which are incorporated herein by reference in their entirety.

FIELD OF THE INVENTION

The present invention relates to a continuous process of making thiocarboxylate-functional silane. More specifically, the present invention relates to the use of a continuous stirred tank reactor and a continuous plug flow reactor and their use in continuously producing thiocarboxylate-functional silanes, such as octanethioic acid S-[3-(triethoxy-silanyl)-propyl]ester, in the presence of a solid-supported phase transfer catalyst.

BACKGROUND OF THE INVENTION

Thiocarboxylate-functional silanes are coupling agents which are used extensively in rubber applications such as tires and tire components. Several batch processes of making thiocarboxylate-functional silane are known. The batch processes include the reactions of alkali metal salts of mercapto-functional silanes with carboxylic acid chlorides or the reactions of alkali metal salts of alkylthioic acids with halo alkyl-containing silanes. The later process, the reactions of alkali metal salts of alkylthioic acids with halo alkyl-containing silanes, are advantageously carried out in a two-phase batch process in which an aqueous phase of the alkali metal salts of alkylthioic acids is reacted with a non-aqueous phase of the halo alkyl-containing silane, often in the presence of phase transfer catalyst. The two-phase batch process eliminates the need to handle solid alkali halide salts, which are a byproduct of the reaction, because these salts are soluble in the aqueous phase.

However, the two-phase batch process has the disadvantages of having to conduct washing of the non-aqueous phase, requiring long reaction times and forming meta-stable rag layers. The washing is needed to remove the phase transfer catalyst from the non-aqueous phase containing the reaction product. The phase transfer catalyst is an undesirable impurity in the product which may affect the curing of the rubber compositions in which the thiocarboxylate-functional silanes are used. The long reaction times results from the diffusion control transport of the alkali metal salts into the non-aqueous phase, and the need to carry out the reaction to completion before the next batch can be started. The meta-stable rag layer, which is an emulsified mixture of water, the reaction products and the phase transfer catalyst, make the separation of the two-phases difficult, often resulting in loss of reaction product.

The use of the two-phase batch process results in the process having the problems of being expensive, long and of limited capacity. Thus, there still exists a need for a process of making thiocarboxylate-functional silane that provides for efficient reaction of a two-phase reaction mixture, reduction of rag layers and very low amounts and advantageously, absence of phase transfer catalysts in the final product.

SUMMARY OF THE INVENTION

The invention is directed to the continuous production of a thiocarboxylate-functional silane coupling agent by utilizing a process that involves two liquid phases and employs a solid-supported catalyst, a continuous stirred tank reactor and a continuous plug flow reactor. The inventive process provides for a continuous production of thiocarboxylate-functional silanes such as octanethioic acid S-[3-(triethoxy-silanyl)-propyl]ester in satisfactory amounts and purity without the limitations of batch processes.

In one embodiment herein there is provided a process for the continuous preparation of thiocarboxylate silane comprising continuously reacting in a continuous plug flow reactor an aqueous phase solution of a salt of a thiocarboxylic acid with a non-aqueous phase haloalkylalkoxysilane in the presence of a solid phase supported catalyst comprising a salt of a positively charged nitrogen-containing functional group. The continuous process for the preparation of a thiocarboxylate silane comprises:

(i) continuously feeding into a plug flow reactor containing a solid phase supported catalyst comprising a salt of a positively charged nitrogen-containing functional group,
   (a) an aqueous liquid phase solution of an ammonium or alkali metal salt of thiocarboxylate acid, and
   (b) a non-aqueous liquid phase haloalkylalkoxysilane;
(ii) continuously contacting the aqueous liquid phase solution of the ammonium or alkali metal salt of thiocarboxylate acid (a) with the non-aqueous liquid phase haloalkylalkoxysilane (b);
(iii) continuously reacting the ammonium or alkali metal salt of thiocarboxylate acid with the haloalkylalkoxysilane to form a non-aqueous liquid phase thiocarboxylate silane and an aqueous liquid phase solution of the ammonium or alkali metal salt of the halide;
(iv) continuously removing from the plug flow reactor the non-aqueous liquid phase thiocarboxylate silane and aqueous liquid phase solution of the ammonium or alkali metal salt of the halide formed in step (iii); and
(v) separating the non-aqueous liquid phase thiocarboxylate silane from the aqueous liquid phase solution of the ammonium or alkali metal salt of the halide formed in step (iv).

In one other embodiment there is provided a process for the continuous preparation of an aqueous solution of an ammonium or alkali metal salt of a thiocarboxylic acid. The process for the continuous preparation of an aqueous liquid phase solution of an ammonium or alkali metal salt of a thiocarboxylic acid comprises:

(i) continuously feeding into a continuously stirred tank reactor an aqueous liquid phase solution of an ammonium or alkali metal salt of a sulfide and/or hydrosulfide;
(ii) continuously feeding into a stirred tank reactor a non-aqueous liquid phase carboxylic acid halide or carboxylic acid anhydride;
(iii) continuously reacting the ammonium or alkali metal salt of a sulfide and/or hydrosulfide of step (i) with the non-aqueous liquid phase carboxylic acid halide or carboxylic acid anhydride of step (ii), optionally in the presence of a catalyst; and
(iv) continuously removing the aqueous liquid phase solution of an ammonium or alkali metal salt of a thiocarboxylic acid from the continuously stirred tank reactor.

In yet one other embodiment there is provided a process for the continuous preparation of thiocarboxylate silane comprising:

(i) continuously reacting in a continuous stirred tank reactor an aqueous liquid phase solution of an ammonium or alkali metal salt of a sulfide and/or hydrosulfide with a carboxylic acid halide and/or carboxylic acid anhydride, optionally in the presence of at least one of a catalyst, to provide a continuous stream of aqueous solution of a salt of a thiocarboxylic acid; and (ii) continuously sending the continuous stream of aqueous liquid phase solution of a ammonium or alkali metal salt of a thiocarboxylic acid to a continuous plug flow reactor containing a solid phase supported catalyst comprising a salt of a positively charged nitrogen-containing functional group, wherein the continuous stream of aqueous liquid phase solution of an ammonium or alkali metal salt of a thiocarboxylic acid is continuously reacted with a non-aqueous liquid phase haloalkylalkoxysilane to provide a continuous stream of thiocarboxylate silane reaction product.

In yet still another embodiment, the process for the continuous preparation of thiocarboxylate silane in carried out in the apparatus shown in FIG. 1, wherein CSTR is a continuous stirred tank reactor.

DETAILED DESCRIPTION OF THE INVENTION

Figure 1:
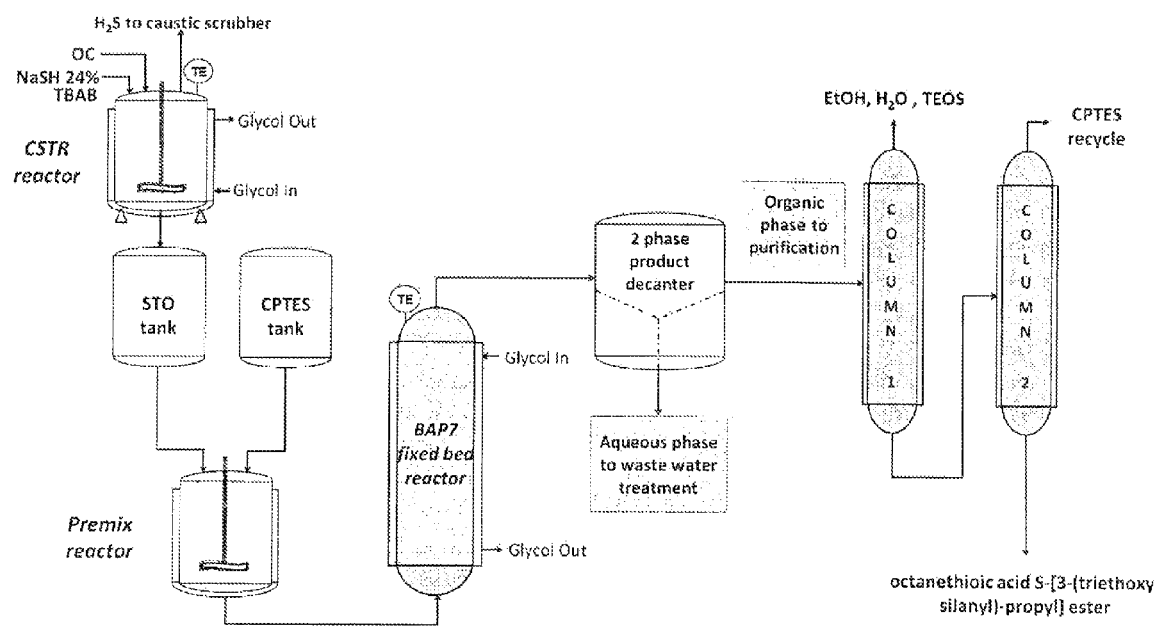
FIG. 1 is a drawing of one embodiment of the apparatus useful in the continuous preparation of thiocarboxylate silanes described herein.
Figure 2:
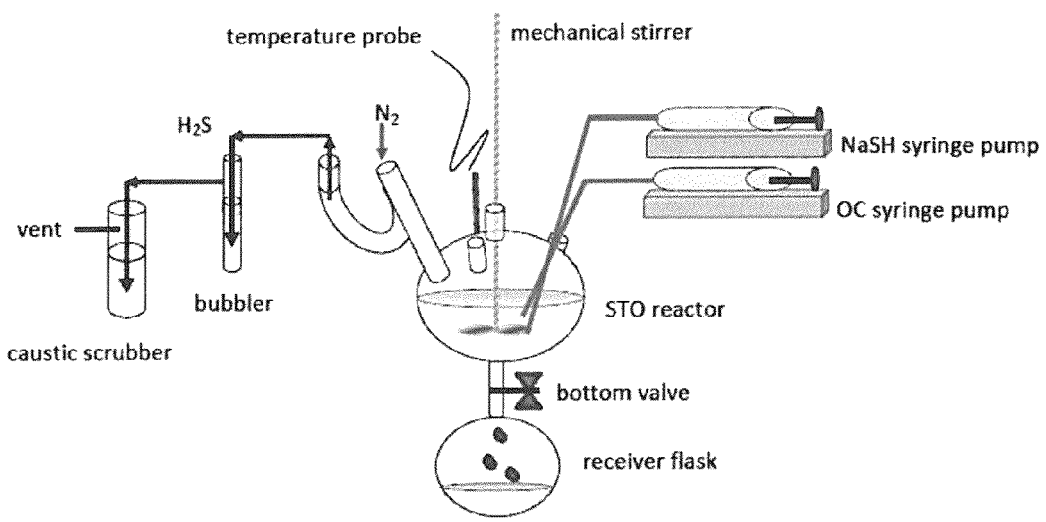
FIG. 2 is a drawing of an apparatus used for the continuous process for making an aqueous solution of sodium thiooctanoate.

The terms "continuous" or "continuously" as used herein are understood as a desirable period of time for conducting the process and/or desirable period of time for conducting a reaction and/or a desired amount of product being produced through a reaction as described herein and can vary in terms of time and/or product produced depending on the reaction being employed and reaction conditions or desired amount of product from the process(es) described herein or desire amount of time of running the process(es) described herein. It will be understood herein that terms "continuous" or "continuously" as used herein can also convey a specific period of time and/or product with a distinct beginning and a distinct end as desired by the user of the process(es) described herein. In another embodiment herein it will be understood herein that the terms "continuous" or "continuously" as used herein are used to reflect other than a batch reaction or an amount of batch product made from a batch reaction using a process involving the same or similar reaction chemistry. In one non-limiting embodiment it shall be understood that terms "continuous" or "continuously" as used herein with respect to a reaction or transport of components, reactants, reaction mixtures, product(s) or byproducts, means uninterrupted extension in time, sequence, or space, i.e., without a break.

Catalyst Used in Plug Flow Reactor

The catalyst used in the plug flow reactor is solid phase supported catalyst comprising a salt of a positively charged nitrogen-containing functional group. The positively charged nitrogen-containing functional group is a pronated amino group, a quaternary ammonium group, a protonated guanidine group or a hexa-alkylated guanidine group. The nitrogen-containing functional group is chemically bonded to the solid support through a carbon-containing linking group or is physic-adsorbed onto the surface of the solid support. The solid support is an organic polymer or an inorganic compound that are not soluble in the liquid aqueous and non-aqueous phases.

The organic polymer solid support may be prepared from the polymerization of monomers containing reactive carbon-carbon double bonds, or polymerization of monomers containing reactive groups to form condensation polymers, such as epoxies, polyesters, polyamides, polyimides, urethanes, polyethers and silicones. Typical monomer containing reactive carbon-carbon double bonds include vinyl containing compounds, such as styrene, vinyl ethers, vinyl esters and olefins, or carbon-carbon double bonds bonded to an ester, amide, nitrile groups. At least one of the monomer used in making the solid support contains a functional group that can be reacted with an amine or guanidine-containing compound or can be reacted with other reactants to form a positively charged nitrogen functional group. It is preferred that the organic polymer support is crosslinked to provide for a support that is insoluble in the aqueous or non-aqueous phases. Insoluble refers to the organic solid support being soluble in the water or octane at less than 1 weight percent solid support per 100 grams water or octane.

Useful inorganic solid supports are siliceous materials, metal oxides, metals, ceramics, minerals that are insoluble in water and octane. Octane is an organic solvent used to determine whether the inorganic solid support is suitable for the application. Insoluble refers to the inorganic solid support being soluble in the water or octane at less than 1 weight percent solid support per 100 grams water or octane. Typical inorganic supports include quartz, clay, aluminum oxide, calcium silicates, glass beads, boron nitride, and the like.

The positively charged nitrogen-containing functional group that is supported on the solid support has the chemical Formula (1):

$$[-R^1N(R^2)_2-R^3]^+X^- \qquad (1)$$

wherein $R^1$ is a divalent alkylene, cycloalkylene, alkenylene, aralkylene, arylene, arenylene group having from 1 to 20 carbon atoms;

each $R^2$ is independently a monovalent alkyl, cycloalkyl, alkenyl, aralkyl, aryl or arenyl group having from 1 to 20 carbon atoms or hydrogen, each $R^3$ is a monovalent alkyl, cycloalkyl, alkenyl, aralkyl, aryl or arenyl group having from 1 to 20 carbon atoms, hydrogen or $-C(=NR^2)-NR^2$ group;

$X^-$ is fluoride, chloride, bromide or iodide.

The positively charged nitrogen-containing functional group may be bonded to the organic solid support through a chemical bond which bonds the $R^1$ group to a carbon atom of the organic polymer backbone or to a heteroatom of nitrogen, oxygen or sulfur which may be part of the organic polymer backbone or part of a functional group pendent to the backbone.

The positively charged nitrogen-containing functional group may be bonded to the inorganic support through a chemical bond which bonds the $R^1$ group to carbon atom, silicon atom, oxygen atom, sulfur atom or nitrogen atom wherein the carbon atom, silicon atom, oxygen atom, sulfur atom or nitrogen atom is bonded to the inorganic solid support. A preferred catalyst comprises an inorganic solid support in which the positively charged nitrogen-containing functional group is bonded to a silicon atom, which in turn is bonded to the solid support through a Si—O—Si bond, Si—O—Fe bond, Si—O—Al bond. Si—O—Mn or Si—O—Cu bond.

A particularly useful catalyst has the general Formula (2):

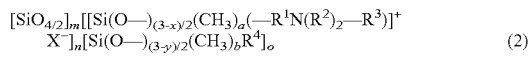

wherein each $R^4$ is independently monovalent alkyl, cycloalkyl, arenyl, aryl or arenyl group containing from 1 to 18 carbon atoms, and optionally containing at least one oxygen, nitrogen or sulfur atom, —OH or —$OR^2$ group, and the values of $R^1$, $R^2$ and $R^3$ are as previously described, m is greater than 1; n is greater than 1; o is greater than 1; x is 0, 1 or 2; and y is 0, 1 or 2.

A particular catalyst of Formula (2) useful in the invention includes m is 50 to 10,000; n is greater than 5 to 500; o is 0 to 500; x is 0, 1 or 2; y is 0, 1 or 2; $R^1$ is methylene, ethylene or propylene; $R^2$ is methyl, ethyl, n-propyl, isopropyl, n-butyl, isobutyl, n-pentyl or n-hexyl; $R^3$ is methyl, ethyl, n-propyl, isopropyl, n-butyl, isobutyl, n-pentyl, n-hexyl, —(C=N(CH$_3$)$_2$N(CH$_3$)$_2$) or —(C=N(CH$_2$CH$_3$)$_2$N(CH$_2$CH$_3$)$_2$); $R^4$ is methyl, ethyl, n-propyl, isopropyl, n-butyl, isobutyl, n-pentyl or n-hexyl, hydroxyl, methoxy, ethoxy, propoxy, isopropoxy, butoxy or pentoxy; and X is chloride or bromide.

Another specific catalyst of Formula (2) includes m is 50 to 10,000; n is greater than 10 to 300; o is 0 to 50; x is 0; y is 0; $R^1$ is propylene; $R^2$ is methyl, ethyl, n-propyl, isopropyl, n-butyl, isobutyl, n-pentyl or n-hexyl; $R^3$ is methyl, ethyl, n-propyl, isopropyl, n-butyl, isobutyl, n-pentyl or n-hexyl; $R^4$ is methyl, ethyl, n-propyl, isopropyl, n-butyl, isobutyl, n-pentyl or n-hexyl, hydroxyl, methoxy, ethoxy, propoxy, isopropoxy, butoxy or pentoxy; and X is chloride or bromide.

In one embodiment herein the catalyst is selected from the group consisting of chloride, tributylammonium propyl, silica; chloride, tributylammonium propyl 2-hydroxyethylsulfide ethyl silica; chloride, tributylammonium propyl dodecylsulfide ethyl silica; bromide, tributylammonium propyl, silica; and combinations thereof.

The catalyst used herein can be added to the plug flow reactor as solid particulates, or as a concentrated or a dilute slurry in water and/or other suitable solvents, such as alcohols. The quantity of catalyst used will depend on the desired rate of reaction and the chemical structure of the catalyst. The solid phase supported catalyst comprising a salt of a positively charged nitrogen-containing functional group should be used in sufficient quantity that the plug flow reactor has catalyst filling the entire radius (width) of the tubular reactor, thereby forcing the reactants to pass through the catalyst bed. Specifically, catalyst is added to fill from 5 to 100 percent of the length of the tubular reactor, more specifically from 50 to 90 percent of the length of the tubular reactor, wherein the percentage is determined by measuring the length of the column of packed, solid supported catalyst in the tubular reactor, where the catalyst occupies the entire width of the tubular reactor, divided by the total length of the tubular reactor and then multiplying that value by 100%.

In one embodiment herein the catalyst has the group, [—$R^1N(R^2)_2$—$R^3$]$^+X^-$, in an amount such that the weight percent amount of the [—$R^1N(R^2)_2$—$R^3$]$^+X^-$ group, based on the total weight of the catalysts is from 3 to 20 weight percent, more specifically from about 4 weight percent to about 18 weight percent and most specifically from about 5 weight percent to about 17 weight percent. A particularly useful catalyst is one in which the [—$R^1N(R^2)_2$—$R^3$]$^+X$ group is propyl tributyl ammonium chloride, and where the amount of the propyl tributyl ammonium chloride group based on the total weight of the catalyst is from 3 weight percent to 20 weight percent, more specifically from 4 weight percent to 18 weight percent and most specifically from 5 weight percent to 17 weight percent. In one embodiment there is more than one propyl tributyl ammonium chloride group per silica component, more specifically from 2 to 5 propyl tributyl ammonium chloride groups, and most specifically from 2 to 3 propyl tributyl ammonium chloride group.

In one further embodiment, the average particle size of the solid supported catalyst employed herein (i.e, the catalyst) is from 50 to 600 micrometers, more specifically from 100 to 550 micrometers and most specifically from 60 to 500 micrometers. Alternatively stated the catalyst has a pore size of from 35 to 220 angstroms, more specifically from 40 to 210 angstroms and most specifically from 45 to 200 angstroms. The particle size is calculated in accordance of STM D4464-10 Standard Test Method for Particle Size Distribution of Catalytic Material by Laser Light Scattering.

Mercury porosity surface area is the specific surface area as determined by the mercury porosimetry method. According to this method, mercury is allowed to penetrate into the pores of a measured sample of particulate filler after a thermal treatment to remove volatiles therefrom. Typical set-up conditions include a 100 mg sample, removing volatiles over a two hour period at 105° C. and ambient atmospheric pressure and a pressure ranging from ambient to 2000 bars. The mercury porosimetry method may be performed in accordance with that described in Winslow, Shapiro in ASTM bulletin, page 39 (1959) or according to DIN 66133. For such a method, a CARLO-ERBA Porosimeter 2000 may be used. The average mercury porosity specific surface area for a typical solid supported catalyst can range from 10 to 300 m$^2$/g.

A suitable pore size distribution for the silica, alumina and aluminosilicate solid supported catalyst according to the foregoing mercury porosity determination method the pore size is from 80 to 110 angstroms.

Silane Structures

The thiocarboxylate silanes, whose continuous preparation by an aqueous route is described herein, may be represented by Formulae 3, 4, and 5:

$$(R^5C(=O)-S-)_aG^2(-SiX_3)_c \qquad (3)$$

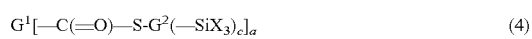

$$G^1[-C(=O)-S-G^2(-SiX_3)_c]_a \qquad (4)$$

$$[G^1(-C(=O)-S-)_a]_b[G^2(-SiX_3)_c]_d \qquad (5)$$

wherein each occurrence of $R^5$ is independently selected from the group consisting of alkyl, cycloalkyl, alkenyl, aryl, arenyl and aralkyl groups containing from 1 to 30 carbon atoms, and hydrogen;

each occurrence of $G^1$ is independently $R^5$ or a polyvalent group (divalent or higher valency) derived from an alkyl, cycloalkyl, alkenyl, aryl, arenyl or aralkyl group containing from 1 to 30 carbon atoms;

each occurrence of $G^2$ is independently a polyvalent group (divalent or higher valency) derived from an alkyl, cycloalkyl, alkenyl, aryl, arenyl or aralkyl group containing from 1 to 30 carbon atoms;

each occurrence of X is independently a member selected from the group consisting of $R^6O$— and —$R^7$, and wherein each $R^6$ and $R^7$ is independently selected from the group consisting of alkyl, cycloalkyl, alkenyl, aryl, arenyl and aralkyl groups containing from 1 to 18 carbon atoms, and hydrogen, wherein at least one X is not —R;

each occurrence of the subscript a is independently an integer from 1 to 6;

each occurrence of the subscript b is independently an integer from 1 to 10;

each occurrence of the subscript c is independently an integer from 1 to 6; and, each occurrence of the subscript d is independently an integer from 1 to 10.

As used herein, alkyl includes straight or branched alkyl groups; alkenyl includes any straight or branched alkenyl group containing one or more carbon-carbon double bonds, where the point of substitution can be either at a carbon-carbon double bond or elsewhere in the group; Specific examples of alkyls include methyl, ethyl, propyl and isobutyl. Specific examples of cycloalkyl includes cyclopentyl, cyclohexyl and cyclooctyl. Specific examples of alkenyls include vinyl, propenyl, allyl and methallyl.

As used herein, aryl includes any aromatic hydrocarbon from which one hydrogen atom has been removed; aralkyl includes any of the aforementioned alkyl groups in which one or more hydrogen atoms have been substituted by the same number of like and/or different aryl (as defined herein) substituents; and arenyl includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl.

As used herein, cycloalkyl, also include bicyclic, tricyclic, and higher cyclic structures as well as the aforementioned cyclic structures further substituted with alkyl or alkenyl groups. Representative examples include norbornyl, norbornenyl, ethylnorbornyl, ethylnorbornenyl, ethylcyclohexyl, ethylcyclohexenyl, cyclohexylcyclohexyl and cyclododecatrienyl.

The key functional group present in the silanes of the present invention is the thiocarboxylate ester group, —C(=O)S— (any silane with this functional group is a "thiocarboxylate ester silane").

Examples of $R^5C(=O)—S—)$ groups include those wherein $R^5$ has a primary carbon attached to the carbonyl and is advantageously a $C_2$-$C_{20}$ straight- or branched-chain alkyl, more particularly a $C_6$-$C_{18}$ straight-chain alkyl. Especially advantageous herein are $C_6$-$C_{14}$ straight-chain alkyls.

Representative examples of $G^1$ and $G^2$ include monovalent groups such as those described above for $R^5$; phenylene; —$(CH_2)_p$— wherein p is 1 to 20, such as —$CH_2$—, —$CH_2CH_2$—, —$CH_2CH_2CH_2$—, —$CH_2CH_2CH_2CH_2$— and —$CH_2CH_2CH_2CH_2CH_2CH_2CH_2CH_2$—; —$CH_2(CH_2)_qCH(CH_3)$— where q is zero to 17, such as —$CH_2CH_2CH(CH_3)$— and —$CH_2CH_2CH_2CH(CH_3)$—; —$CH_2CH_2C(CH_3)_2CH_2$—; —$CH_2CH(CH_3)CH_2$—; —$CH_2CH_2(C_6H_4)CH_2CH_2$— and —$CH_2CH_2(C_6H_4)CH(CH_3)$— where the notation $C_6H_4$ denotes a disubstituted benzene ring; —$CH_2CH(CH_3)(C_6H_4)CH(CH_3)CH_2$— where the notation $C_6H_4$ denotes a disubstituted benzene ring; —$CH_2CH(CH_2CH_3)$—; —$CH_2CH_2CH(CH_2CH_3)$—; —$CH_2CH(CH_2CH_3)$—; —$CH_2CH(CH_3)CH_2CH_2$—; —$CH_2CH(CH_3)CH(CH_3)$—; —$CH_2C(CH_3)(CH_2CH_3)$—; —$CH_2CH_2CH(CH_3)CH_2$—; —$CH_2CH_2C(CH_3)_2$—; —$CH_2CH[CH(CH_3)_2]$—; —$CH_2CH_2$—$C_6H_{10}$— where the notation $C_6H_{10}$ denotes any isomer of the disubstituted cyclohexane ring; $C_6H_9(CH_2CH_2—)_3$—$CH_2CH_2(vinylC_6H_9)CH_2CH_2$— and —$CH_2CH_2(vinylC_6H_9)CH(CH_3)$— where the notation $C_6H_9$ denotes any isomer of the trisubstituted cyclohexane ring.

Some specific structures for $G^2$ are —$CH_2$—, —$CH_2CH_2$—, —$CH_2CH_2CH_2$—, $CH_2CH(CH_3)CH_2$— The structure —$CH_2CH_2CH_2$— is particularly advantageous.

Representative examples of $R^5$ groups include methyl, ethyl, propyl, isopropyl butyl, pentyl, n-hexyl, n-octyl, n-decyl, n-dodecyl, benzyl and tolyl. Some specific $R^6$ groups are $C_1$ to $C_4$ alkyls and hydrogen. A specific example of $R^7$ is methyl.

Representative examples of X are methoxy, ethoxy, isobutoxy, propoxy and isopropoxy. Ethoxy is particularly advantageous.

Included among the embodiments herein are those in which X is $R^5O$— is any of methyl, ethyl, propyl, butyl or isopropyl; and, $G^1$ is a $C_6$ to $C_{10}$ straight-chain alkyl group $G^2$ is a $C_2$ to $C_{20}$ straight-chain alkylene chain. Other specific embodiments include structures of Formula 4, wherein the structure has the specific formula $X_3SiG^2SC(=O)G^1C(=O)SG^2SiX_3$, where $G^2$ is a $C_1$ to $C_3$ straight-chain alkylene, and $G^1$ is a $C_1$ to $C_6$ alkylene, $C_2$ to $C_6$ alkenylene or phenylene, and X is $R^5O$— or $R^6$.

Specific embodiments include those wherein X is ethoxy and $G^1$ is a $C_6$-$C_4$ straight-chain alkyl.

Representative examples of the silanes whose continuous preparation is described in the present invention include 2-triethoxysilyl-1-ethyl thioacetate; 2-trimethoxy-silyl-1-ethyl thioacetate; 2-(methyldimethoxysilyl)-1-ethyl thioacetate; 3-trimethoxy-silyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxy-silyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxy-silyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate, also known as 3-trimethoxysilyl-1-propyl thioloctoate and 3-trimethoxysilyl-1-propyl thiocaprylate; 3-triethoxysilyl-1-propyl thiopalmitate; 3-triethoxysilyl-1-propyl thiooctanoate, also known as 3-octanoylthio-1-propyltriethoxy silane, 3-triethoxysilyl-1-propyl thioloctoate and 3-triethoxysilyl-1-propyl thiocaprylate; 3-triethoxysilyl-1-propyl thiodecanoate; 3-triethoxysilyl-1-propyl thiododecanoate, also known as 3-triethoxysilyl-1-propyl thiolaurate; 3-triethoxysilyl-1-propyl thiotetradecanoate, also known as 3-triethoxysilyl-1-propyl thiomyristate; 3-triethoxysilyl-1-propyl thiobenzoate; 3-triethoxysilyl-1-propyl thio-2-ethylhexanoate; 3-triethoxysilyl-1-propyl thio-2-methylheptanoate; bis-(3-triethoxysilyl-1-propyl)dithiophthalate; bis-(3-triethoxysilyl-1-propyl)dithio-iso-phthalate; bis-(3-triethoxysilyl-1-propyl)dithio-tere-phthalate; bis-(3-triethoxysilyl-1-propyl)dithiosuccinate; bis-(3-triethoxysilyl-1-propyl)dithiooxalate; bis-(3-triethoxysilyl-1-propyl)dithiosebacate; and, bis-(3-triethoxysilyl-1-propyl)dithioadipate.

The thiocarboxylate silane compositions included herein may be prepared as various mixtures of individual thiocarboxylate silane components, optionally including other species as well, including wherein synthetic methods result in a distribution of various silanes and including wherein mixtures of the starting components are employed for the purpose of generating mixtures of thiocarboxylate silane products. Moreover, it is understood that the partial hydrolysates and/or condensates of these thiocarboxylate silanes (i.e., thiocarboxylate siloxanes and/or silanols) may also be encompassed by the thiocarboxylate silanes herein, in that these partial hydrolysates and/or condensates will be a side product of most methods of manufacture of the thiocarboxylate silanes or can occur upon storage of the thiocarboxylate silanes, or under conditions in which residual water remaining from their preparation is not completely removed subsequent to their preparation.

Preparation of Thiocarboxylate Silane

The process herein for the continuous preparation of thiocarboxylate-functional silane (i.e., the product) involves the continuous reaction in a continuous plug flow reactor between aqueous solution of a salt of thiocarboxylic acid (i.e., an aqueous solution containing thiocarboxylate anion) with a haloalkylalkoxysilane in the presence of a catalytically effective amount of a solid phase supported catalyst comprising a salt of a positively charged nitrogen-containing functional group. Optionally, mixtures of aqueous thiocarboxylate salts and/or haloalkylalkoxysilanes can be used in which case mixtures of thiocarboxylate silanes will be obtained.

As used herein, the expression "haloalkylalkoxysilane" refers to any silane whose structure can be represented by Formula (6):

wherein $G^2$ is a polyvalent group derived from an alkyl, cycloalkyl, alkenyl, aryl, arenyl or aralkyl group containing from 1 to 30 carbon atoms;

each occurrence of X is independently a member selected from the group consisting of $R^6O$— and —$R^7$, and wherein each $R^6$ and $R^7$ is independently selected from the group consisting of alkyl, cycloalkyl, alkenyl, aryl, arenyl and aralkyl groups containing from 1 to 18 carbon atoms, and hydrogen, wherein at least one X is not —R;

c is an integer from 1 to 6;

L is a chloro, bromo or iodo; and f is an integer from 1 to 6. Thus, "haloalkylalkoxysilane" includes silanes with one or more halogen substitutions for hydrogen on their hydrocarbon groups.

As used herein, the expression, "thiocarboxylate salts" refers to any ammonium or alkali metal salt of a thiocarboxylate anion whose structure can be represented by Formula (7)

wherein $G^1$ is $R^5$ or a polyvalent group (divalent or higher valency) derived from an alkyl, cycloalkyl, alkenyl, aryl, arenyl or aralkyl group containing from 1 to 30 carbon atoms, wherein $R^5$ is independently selected from the group consisting of alkyl, cycloalkyl, alkenyl, aryl, arenyl and aralkyl groups containing from 1 to 30 carbon atoms, and hydrogen;

$M^+$ is ammonium group selected from $NH_4^+$, $NR^2H_3^+$, $NR^2_2H_2^+$, $NR^2_3H^+$ and $NR^2_4^+$ or an alkali metal cation; and the subscript a is an integer from 1 to 6.

Representative examples of $M^4$ are sodium, potassium, calcium, ammonium, methyl ammonium, triethyl ammonium and tetramethylammonium. Sodium and potassium cations are especially advantageous.

Haloalkylalkoxysilane reactants for use herein include 3-chloromethyl-1-triethoxysilane, 3-chloroethyl-1-triethoxysilane, 3-chloropropyl-1-triethoxysilane and 3-chlorobutyl-1-triethoxysilane. Of these, 3-chloropropyl-1-triethoxysilane is particularly advantageous.

The chemical equation(s) for the continuous reaction(s) between the aqueous thiocarboxylate salt(s) and the haloalkyl silane(s) to yield the thiocarboxylate silane(s) (e.g., the continuous stream of thiocarboxylate silane reaction product) is (are) represented by Equations I, II, and III as follows:

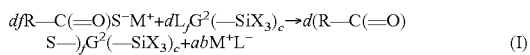

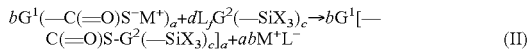

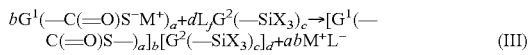

wherein each of R, $G^1$, $G^2$, Y, L, X, and $M^+$ are as defined herein and "a" "b", "c" and "d" in equations (I), (II) and (III) above, are the relative molar amounts of the respective reaction components.

The continuous preparation of the product thiocarboxylate silane in accordance with the invention is carried out by combining and reacting haloalkyl silane and aqueous solution of thiocarboxylate salt in the presence of the solid phase supported catalyst comprising a salt of a positively charged nitrogen-containing functional group described herein, usually accompanied by agitation, e.g., stirring, as described below in the premix reactor of the two reactants, followed by continuous feeding the reactants to the plug flow reactor containing the solid phase supported catalyst comprising a salt of a positively charged nitrogen-containing functional group and forcing the reactants through the continuous plug flow reactor, until the reaction has reached the desired level of completeness and/or the desired amount of product has been obtained over a period of continuous use of the process(es) described herein.

Additional salt(s) may optionally be present or be added to the aqueous solution of a salt of thiocarboxylic acid to increase the ionic strength of the solution so as to further stabilize the product silane(s) against hydrolysis. Examples of such additional salts include alkali metal salts such as the sodium and potassium halides and the corresponding carbonates and nitrates. These and similar salts can be present in the reaction medium at a level of up to 50, and advantageously up to about 20 weight percent of the amount of thiocarboxylate salt reactant present therein.

The level of completeness of the various continuous reactions described herein can be monitored by any means which distinguishes the reactants from the products, such as, for example, gas chromatography (GC), liquid chromatography (LC or HPLC), nuclear magnetic resonance spectroscopy (NMR), or infrared spectroscopy (IR) of the organic phase, or wet chemical analysis of the aqueous phase.

Suitable reaction conditions for the continuous reactions described herein include temperatures of from −5° C. to 150° C. and pressures of ambient to 100 atmospheres or vacuum from ambient to 0.01 torr. Specific embodiments include conditions of from about 0° C. to 100° C. and at ambient pressure. Additional embodiments include reaction temperatures of from 25° C. to 95° C., and advantageously from 40° C. to 90° C. or from 20° C. to 35° C. Variable temperatures within the aforementioned ranges may be employed, as, for example, a gradual upward or downward ramping of the temperature during the course of the reaction. In one embodiment herein the reaction period for the continuous process of reacting the haloalkylalkoxysilane and aqueous solution of a salt of thiocarboxylate silane can be from 2 to 12 hours, more specifically from 5 to 7 hours.

In one embodiment herein the process for the continuous preparation of thiocarboxylate silane comprises continuously reacting an aqueous solution of an ammonium or alkali metal salt of a thiocarboxylic acid with a haloalkylalkoxysilane in the presence of a solid supported catalyst comprising a salt of a positively charged nitrogen-containing functional group in a continuous plug flow reactor.

In a more specific embodiment, the continuous plug flow reactor is a continuous tubular plug flow fixed bed reactor or a tubular packed reactor. Specifically the continuous tubular plug flow reactor has a ratio of internal diameter to length of from 3 to 100, more specifically of from 5 to 35.

Representative continuous plug flow reactor may have a diameter of from 1 to 5 cm and a length of from 15 to 100 cm or the continuous plug-flow reactor has an internal diameter of from 2 to 4 cm and a length of from 20 to 30 cm. Larger diameter and longer length reactors can be used if higher production rates are desirable.

The amount of catalyst employed in the continuous plug flow reactor having a diameter of from 1 to 5 cm and a length of from 15 to 100 cm can advantageously be from 50 to 100 grams in the continuous plug-flow reactor, more specifically from about 60 to about 75 grams, or any other amounts which would be suitable to the scaled version of the continuous process or the scaled version of the specific continuous tubular plug flow reactor being employed in the process.

In one non-limiting embodiment herein the continuous plug flow reactor having a diameter of from 1 to 5 cm and a length of from 15 to 100 cm when employed in the process(es) described herein can have an average contact time in a single pass of from 5 to 40 minutes more specifically from 6 to 35 minutes and most specifically from 7 to 33 minutes, or any other contact times which would be suitable to the scaled version of the continuous process or scaled version of the specific continuous tubular plug flow reactor being employed in the process.

In one non-limiting embodiment herein the process can have a space velocity σ of from 0.01 to 0.20 minutes$^{-1}$, more specifically of from 0.02 to 0.18 minute$^{-1}$ and most specifically of from 0.03 to 0.15 minute$^{-1}$. Space velocity refers to the quotient of the entering volumetric flow rate of the reactants divided by the reactor volume (or catalyst bed volume), which indicates how many reactor volumes of feed can be treated in a unit time. By definition, space velocity can be expressed mathematically as σ=υ0/V. In this expression, υ0 represents the volumetric flow rate of the reactants entering the reactor and V represents the volume of the reactor itself. The space velocity is measured at a set of standard conditions.

The continuous plug flow reactor can be configured as a catalytic reactor, fixed bed reactors or a packed bed reactor. The continuous plug-flow reactor is tubular reactor. The continuous plug-flow reactor can be jacketed or contain a coil or other means to provide for temperature control to the suitable temperatures described herein. The continuous plug flow reactor can contain static mixers to facilitate mixing of the two liquid phases of the reactants. Continuous plug flow reactors can be custom built or obtained from Holloway America, Technolab Equipment, or Hitech Technologies.

In one embodiment the process of continuously reacting the aqueous solution of salt of a thiocarboxylic acid with a haloalkylalkoxysilane in the presence of a catalyst in the continuous plug flow fixed bed reactor is such that a continuous stream of thiocarboxylate silane reaction product is recycled into the continuous plug-flow reactor at least one time prior to being sent to a continuous phase separator, more specifically at least from 5 to 10 times, and most specifically from 5 to 7 times.

Ordinarily, and by way of reducing the amount of siloxane-type by-product(s) that may be formed during the continuous thiocarboxylate silane-forming reaction, it is advantageous to conduct this reaction by first premixing the reactants under continuous agitation, e.g., that provided by the motion of a conventional rotary stirrer such as the premix reactor described herein. The vigorousness of the agitation will ordinarily be such as to keep the amount of siloxane-type by-product(s) produced during the continuous thiocarboxylate silane-forming reaction to within reasonable bounds, e.g., less than 20 weight percent, more commonly less than 12 weight percent, and typically to within 5 to 10 weight percent, of the total amount of reaction product. The amount of agitation required to achieve this can be determined in a specific case by routine experimentation.

Suitable concentrations of the starting aqueous solution of a salt of a thiocarboxylic acid are from 1 weight percent up to saturation, which can be as high as 50 weight percent or more. Particular concentrations include from 20 to 45 weight percent and from 30 to 40 weight percent, with the understanding that the remaining weight percentages amounts are the amount(s) of water in the aqueous solution of a salt of a thiocarboxylic acid. Optionally, an excess of the thiocarboxylate salt relative to that demanded by the reaction stoichiometry may be used to drive the reaction to completion so as to obtain a product of minimal residual haloalkylalkoxysilane starting material, to obtain the product with minimal reaction time and/or temperature, and/or to obtain a product with minimal loss to, or contamination by, silane hydrolysis/condensation products. Alternatively, an excess of the haloalkylalkoxysilane relative to that demanded by the reaction stoichiometry may be used to reduce the residual aqueous solution of a salt of a thiocarboxylic acid content at the completion of the reaction to a minimum. In one embodiment, the amount of aqueous solution of thiocarboxylate salt can be present in the reaction medium in an amount of from 55 weight percent to 80 weight percent, more specifically from 68 weight percent to 75 weight percent. The amount of haloalkylalkoxysilane reactant can be present in the reaction medium in an amount of from 20 weight percent to 45 weight percent, more specifically from 24 weight percent to 30 weight percent.

The continuous reactions described herein may be run in which the haloalkylalkoxysilane is not diluted in an organic solvent (i.e., the haloalkylalkoxysilane is added neat to the continuous plug-flow reactor) or in the presence of solvents which are insoluble or have limited solubility in water, where limited solubility refers to having a solvent that is soluble in water at less than 2 weight percent of the solvent, based on the total weight of the solvent and the water. Examples of appropriate solvents are ethers, for example, diethyl ether, hydrocarbons, for example, hexane, petroleum ether, toluene, and xylene; and ketones, for example, methyl ethyl ketone. Toluene or xylene are particularly advantageous. It is frequently advantageous to run the reactions neat.

In the reactions described herein, which are understood to be continuous, the process comprise sending of the continuous stream of thiocarboxylate silane reaction product to a phase separator and separating the stream of thiocarboxylate silane reaction product into two liquid phases, the organic phase contains the thiocarboxylate silane product and the waste aqueous phase contains the coproduced salts plus any salts initially present or subsequently added to increase the ionic strength of the reaction medium. In one embodiment, the process can comprise continuously sending of the continuous stream of thiocarboxylate silane reaction product to a continuous phase separator and continuous separating the stream of thiocarboxylate silane reaction product into two liquid phases, the organic phase contains the thiocarboxylate silane product and the waste aqueous phase contains the coproduced salts plus any salts initially present or subsequently added to increase the ionic strength of the reaction medium.

If a starting aqueous solution of sufficient concentration is used, a solid phase comprised of precipitated or crystallized salts may also separate. These salts may optionally be dissolved by addition of water so as to obtain a mixture made up of mainly or exclusively of two liquid phases. These phases can also be separated by the continuous phase separator. Any solvents used during the process may then be removed by distillation or evaporation in the subsequent separatory column(s). Residual water may be removed by vacuum and/or heat stripping as described herein in the separatory column(s). Residual particulates may subsequently or concurrently be removed by further filtration. Residual haloalkylalkoxysilane may be removed by stripping under vacuum at elevated temperature as described herein in the separatory column(s).

In one embodiment, the continuous phase separator is a two-phase product decanter. In one embodiment the aqueous phase separated in the two-phase product decanter is continuously sent to waste water treatment, while the separated organic phase is continuously sent to the at least one separatory column described herein.

In one non-limiting embodiment, the two-phase product decanter may be the model Decantor CC 450 or CB 635 obtained from GEA Westfalia Separator Group, or model decantors Baby, Series 1, 2 or 3. Jumbo, Series 1, 2, 3 or 4, FP 600 or Giant. Series 2, 3, IIL or III, obtained from Gruppo Pieralisi, Dedicated Innovators, Division Separation Solutions.

In one embodiment, the continuous stream of thiocarboxylate silane reaction product is continuously sent from the continuous plug flow reactor to the continuous phase separator such that the phase separation being conducted in the continuous phase separator is continuous.

The continuous process of making thiocarboxylate silane herein can further comprise sending the separated organic phase continuously separated in the continuous phase separator to at least one separatory column and continuously removing byproducts and/or unreacted haloalkylalkoxysilane in the at least one separatory column. The byproducts that can be removed are for example, alkanol, water and tetraalkylorthosilicate(s) (e.g., ethanol, water and tetraethylorthosilicate). The reactants that can be removed are haloalkylalkoxysilane, such as the non-limiting example of 3-chloropropyltriethoxysilane.

In one non-limiting embodiment the at least one separatory column comprises at least two separatory columns in series wherein a first separatory column operating at a first temperature and a first vacuum removes at least one of alkanol, water and tetraalkylorthosilicate and a second separatory column operating at a second temperature and a second vacuum which are higher than the first temperature and first vacuum wherein the second separatory column removes unreacted haloalkylalkoxysilane. In one embodiment, the temperature of the first separatory column is from 15° C. to about 160° C. and a pressure of from 0.0015 newton/square millimeter to about 0.1 newton/square millimeter ($N/mm^2$) and the temperature in the second separatory column is from 80° C. to 230° C. and a pressure of from the vacuum is from 0.0015 newton/square millimeter to about 0.1 newton/square millimeter. The rate of feed from the continuous phase separator to the at least one separatory column is such that the rate of removal of byproducts and/or unreacted haloalkylalkoxysilane in the at least one separatory column is continuous.

In one embodiment herein the at least one separatory column is continuous distillation column obtainable from J. D. Cousins, or obtainable from Innovative Engineers.

In one embodiment, the aqueous solution of a salt of a thiocarboxylic acid and the haloalkylalkoxysilane are first continuously premixed in a premix reactor. The premix reactor is used with a stirring speed such that the tip speed of the stirrer should be at least 60 centimeters per second, advantageously at least 75 centimeters per second with at least 85 centimeters per second providing especially good results. The premix reactor can be continuously used such that the haloalkylalkoxysilane is dispersed within the aqueous solution of thiocarboxylate salt to form small droplets, which aid in the continuous movement of the two liquid phases to the continuous plug flow reactor. In one embodiment the premix reactor can contain a catalyst. Illustrative examples of the catalyst include a homogenous catalyst such as the non-limiting example of tetrabutyl ammonium bromide.

In one embodiment the premix reactor is continuous stirred reactor or special mixing vessel from Pope Solution Driven.

In one embodiment, the aqueous solution of a salt of a thiocarboxylic acid and the haloalkylalkoxysilane are continuously sent to the premix reactor from two separate vessels wherein one of the separate vessels contains and/or is continuously fed with the aqueous solution of a salt of a thiocarboxylic acid and the other of the two separate vessels contains and/or is continuously fed with the haloalkylalkoxysilane. In one embodiment, the separate vessel containing the aqueous solution of a salt of a thiocarboxylic acid is continuously fed from the continuous stirred reactor described herein. The rate of the continuous feed of the aqueous solution of a salt of a thiocarboxylic acid and the rate of the continuous feed of the haloalkylalkoxysilane is such that it provides a continuous stream of reactants to the premix reactor and the rate of the continuous feed of the premixed reactants in the premix reactor to the continuous plug flow reactor is such that the reaction of aqueous solution of a salt of a thiocarboxylic acid and haloalkylalkoxysilane in the continuous plug flow reactor is continuous.

The process of making thiocarboxylate silane is conducted in a continuous manner such that in one non-limiting embodiment, the catalyst(s) is recycled to the process, such as in one example, by filtering the catalyst using known means and then optionally washing the catalyst with water and then recycling the catalyst to fresh reactants in the continuous process.

Alternatively, in one embodiment, the catalyst from the continuous production of the aqueous thiocarboxylate salt reactant (as described below) can be also employed in the continuous process of making the thiocarboxylate silane.

Preparation of Aqueous Thiocarboxylate Salt Reactant

If an aqueous solution of the thiocarboxylate salt(s) required for the preparation of the thiocarboxylate silane composition is not available, it may be prepared in a separate portion of the same overall continuous process in a continuous step preceding its continuous use in the preparation of the thiocarboxylate silane composition, e.g., the aqueous thiocarboxylate salt may be prepared in situ and used directly thereafter, as described above, to continuously prepare the thiocarboxylate silane composition. Alternatively the preparation of aqueous solution of thiocarboxylate salt and the preparation of thiocarboxylate silane composition may be separate continuous processes.

If the thiocarboxylate salt is available, the aqueous solution thereof can simply be prepared by dissolving the appropriate amount of the salt into the appropriate amount of water to provide a solution of the desired concentration, or it can be prepared by dilution or evaporative concentration of whatever solution is available. Alternatively, the desired thiocarboxylate salt or aqueous solution thereof can be prepared from another salt of the desired thiocarboxylic acid. If the thiocarboxylic acid is available, the thiocarboxylate salt or aqueous solution thereof can be prepared simply by neutralizing the acid with a suitable base.

However, if neither the desired thiocarboxylic acid or one of its salts is available, it can be prepared by synthesis of the thiocarbonyl group by continuous reaction of the appropriate acid halide and/or acid anhydride (e.g., the acid chloride) with an aqueous solution of a sulfide, a hydrosulfide, or mixture thereof (e.g., aqueous sodium hydrosulfide, NaSH), to yield a continuous stream of aqueous solution of the thiocarboxylic acid salt. If an aqueous mixture of thiocarboxylate salts is desired, the component thiocarboxylate salts can be blended, or the appropriate mixture of acid halides and/or acid anhydrides can be used in the preparation of the thiocarboxylate salts. Mixtures of one or more acid halides and acid anhydrides can optionally be used, as can mixtures of different sulfides and/or hydrosulfides when preparing either single-component or mixtures of aqueous thiocarboxylate salts.

Structures for the sulfides, hydrosulfides, and carboxylic acid halides are represented by Formulae 8, 9, and 10, respectively.

$$M^+_2 S^{-2} \quad (8)$$

$$M^+ SH^- \quad (9)$$

$$G^1(-C(=O)-L^1)_a \quad (10)$$

wherein
each occurrence of $M^+$ is an ammonium group selected from $NH^+_4$, $NR^2H^+_3$, $NR^2_2H^+_2$, $NR^2_3H^+$ and $NR^2_4{}^+$ or an alkali metal cation, where each occurrence of $R^2$ is independently a monovalent alkyl, cycloalkyl, alkenyl, aralkyl, aryl or arenyl group having from 1 to 20 carbon atoms;
each occurrence of $L^1$ is a halogen atom (i.e., F, Cl, Br, or I) or carboxylate group;
each occurrence of $G^1$ is independently $R^5$ or a polyvalent group derived from an alkyl, cycloalkyl, alkenyl, aryl, arenyl or aralkyl group containing from 1 to 30 carbon atoms, wherein $R^5$ is independently selected from the group consisting of alkyl, cycloalkyl, alkenyl, aryl, arenyl and aralkyl groups containing from 1 to 30 carbon atoms and hydrogen; and
each occurrence of the subscript a is independently an integer from 1 to 6.

$M^+$ is typically a monocation, meaning it occurs as a cation, typically with a single positive charge. Dicationic ions could also be used in cases where their sulfides or hydrosulfides are available, suitably stable, and are sufficiently soluble in water. As such, $M^{+2}$ is the counterion to the anionic sulfide or hydrosulfide anion. Representative examples of $M^+$ are sodium, potassium, ammonium, methyl ammonium, and triethyl ammonium. Sodium, potassium, and ammonium are especially advantageous.

$L^1$ is a halogen atom or carboxylate group. Representative examples of $L^1$ are chloride, bromide, and any carboxylate, such as acetate, octanoate, decanoate, and dodecanoate. $L^1$ could even be a divalent group, such as sulfate or phosphate. Specific embodiments include those where $L^1$ is chloride or carboxylate with chloride being particularly advantageous. In the case where $L^1$ is chloride, the reagent is a carboxylic acid chloride. Where $L^1$ is carboxylate, the reagent is a carboxylic acid anhydride.

In the descriptions which follow, of the procedures for the preparation of aqueous thiocarboxylate salt solutions, it is to be understood, herein, that the term carboxylic acid halide shall refer to the carboxylic acid fluoride, carboxylic acid chloride, carboxylic acid bromide, carboxylic acid iodide, carboxylic acid anhydride, or mixed carboxylic acid anhydride with another carboxylic acid, or any mixture thereof; and that the term sulfide shall refer to an ammonium or alkali metal cation; and the term thiocarboxylate salt, shall refer to a single-component or mixture of salts of one or more than one thiocarboxylate and/or counterion (cation).

Chemical equations for continuous reactions between the aqueous sulfides and/or hydrosulfides and the acid halides and/or acid anhydrides to yield the aqueous thiocarboxylate salts are illustrated by Equations IV, V, VI, and VII.

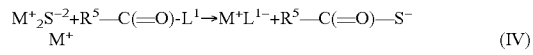

$$M^+_2 S^{-2} + R^5-C(=O)-L^1 \rightarrow M^+L^{1-} + R^5-C(=O)-S^-M^+ \quad (IV)$$

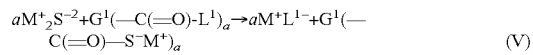

$$aM^+_2 S^{-2} + G^1(-C(=O)-L^1)_a \rightarrow aM^+L^{1-} + G^1(-C(=O)-S^-M^+)_a \quad (V)$$

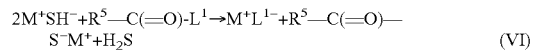

$$2M^+SH^- + R^5-C(=O)-L^1 \rightarrow M^+L^{1-} + R^5-C(=O)-S^-M^+ + H_2S \quad (VI)$$

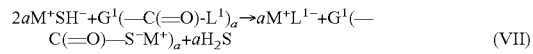

$$2aM^+SH^- + G^1(-C(=O)-L^1)_a \rightarrow aM^+L^{1-} + G^1(-C(=O)-S^-M^+)_a + aH_2S \quad (VII)$$

where M, $R^5$, $L^1$ and $G^1$ are as defined herein and "a" is defined as the relative molar amount of the respective reaction component.

The preparation of the aqueous solution of thiocarboxylate salt in one embodiment is carried out by continuous addition of the carboxylic acid halide and/or carboxylic acid anhydride to an aqueous solution of the sulfide and/or hydrosulfide and agitating the mixture as described herein, e.g., in the continuous stirred tank reactor. Due to the corrosive properties of the carboxylic acid halide and/or carboxylic acid anhydride, practical considerations suggest that this reaction be carried out in glass or in a glass-lined reactor or in a reactor that is constructed of metals that are resistant to halides, such as Hastelloy®.

In one embodiment herein the continuous reaction of an aqueous solution of a sulfide and/or hydrosulfide with an carboxylic acid halide and/or carboxylic acid anhydride can occur in a continuous stirred tank reactor in the absence or presence of a catalyst used in the plug flow reactor, such as a solid phase supported catalyst comprising a salt of a positively charged nitrogen-containing functional group, or a phase transfer catalyst, such as tetra-alkyl ammonium halides or hexa-alkyl guanidine halides, to provide a continuous stream of aqueous solution of thiocarboxylic acid salt.

Since the continuous thiocarboxylate salt-forming reaction is fast and exothermic, it is advantageous to employ a reactor, such as the continuous stirred tank reactor described herein, having temperature control capability, e.g., a jacket or coil through which a coolant such as chilled water or brine is circulated at an adjustable rate. In the absence of such temperature control capability, one can maintain the desired reaction temperature by controlling the rate of addition of the carboxylic acid chloride reactant to the mixture of aqueous sulfide/hydrosulfide and catalyst. The continuous stirred tank reactor can be cooled to maintain a reaction temperature below 100° C., and more specifically from 20° C. to 35° C.

In one embodiment the continuous stirred tank reactor obtained from Pfaudler Process Solution Group, Engineered Systems or Resun Manufacturing Company.

In one embodiment the aqueous solution of a sulfide and/or hydrosulfide and the carboxylic acid halide and/or acid anhydride are continuously added at a fixed rate to the continuous stirred tank reactor and the continuous stream of aqueous solution of thiocarboxylic acid salt and $H_2S$ are continuously removed from the continuous stirred tank reactor at a fixed rate wherein the rate of addition and removal are such that the reaction is continuous.

In another embodiment herein prior to the commencement of the continuous reaction in the continuous stirred tank reactor, the aqueous solution of a sulfide and/or hydrosulfide and the carboxylic acid halide and/or acid anhydride are provided to the continuous stirred tank reactor until the contents of the continuous stirred reactor occupy a desired volume of from 50 to 90 percent of the volume of the continuous stirred reactor. In one embodiment the continuous stirred tank reactor contains a homogenous catalyst such as tetrabutyl ammonium bromide.

In one embodiment when the contents of the continuous stirred reactor occupy the desired volume and the continuous reaction of the aqueous solution of a sulfide and/or hydrosulfide with a carboxylic acid halide and/or acid anhydride has been commenced, a continuous stream of aqueous solution of a salt of a thiocarboxylic acid and a continuous stream of a haloalkylalkoxysilane are then continuously fed to the premix reactor. In one embodiment, the haloalkylalkoxysilane is added to the premix reactor simultaneously with the aqueous solution of a salt of a thiocarboxylic acid from the continuous stirred tank reactor. In one embodiment, the continuous process can comprises wherein prior to being fed to the premix reactor the aqueous solution of a salt of a thiocarboxylic acid from the continuous stirred tank reactor is continuously fed to a separate tank from which the aqueous solution of a salt of a thiocarboxylic acid is then continuously fed to the premix reactor simultaneously or alternatively with the continuous feeding of haloalkylalkoxysilane from a haloalkylalkoxysilane holding tank. Then the contents of the premix reactor can be continuously premixed and continuously sent to the continuous plug flow reactor wherein the continuous stream of aqueous solution of a salt of a thiocarboxylic acid undergoes the continuous reaction with the haloalkylalkoxysilane. Then the continuous process can further undergo the steps outlined herein such as the further steps in producing the thiocarboxylate silane described herein.

The catalyst, as described herein (solid supported catalyst comprising a salt of a positively charged nitrogen-containing functional group or a phase transfer catalyst described herein) may be added in one or several doses and/or in a continuous manner to the aqueous sulfide/hydrosulfide solution, the carboxylic acid halide/acid anhydride, and/or the continuous reaction mixture before, during, and/or after the addition of the carboxylic acid halide/acid anhydride to the aqueous sulfide/hydrosulfide solution to accelerate the reaction. In an alternate embodiment, the catalyst used in the continuous preparation of the aqueous thiocarboxylate salt is a homogenous phase transfer catalyst (i.e., a non-solid-supported catalyst) such as the non-silica containing catalysts such as hexaethylguanidine chloride and/or tributylammonium bromide, and/or tetrabutylammonium bromide, and the like, as are well known in the art. In a further embodiment, the catalyst used in the continuous preparation of the aqueous thiocarboxylate salt is a mixture of a homogenous catalyst and the solid supported catalyst comprising a salt of a positively charged nitrogen-containing functional group the described herein for the continuous reaction between the aqueous thiocarboxylate salt and the haloalkylalkoxysilane.

Appropriate reaction conditions for the aqueous thiocarboxylate salt-forming continuous reaction include temperatures of from 10° C. to 40° C., and advantageously and from 20° C. to 50° C., and advantageously from 25° C. to 40° C., for continuous operation in order to minimize or suppress by-product formation. In one embodiment the continuous aqueous thiocarboxylate salt-forming reaction can be conducted over a period of time ranging from 1 to 3 hours.

Additional conditions of the continuous process for making the aqueous thiocarboxylate salt include a pressure of from 0.01 torr to 100 atmospheres, advantageously from 100 torr to 2 atmospheres, and a molar ratio of sulfide/hydrosulfide to carboxylic acid chloride/acid anhydride of from 2:1 to 3:1, and advantageously from 2:1 to 2.2:1. The continuous process is advantageously carried out with agitation of the reaction medium, e.g., employing a continuously stirred tank reactor, to minimize the formation of undesirable by-product(s). In general and when employing a continuously stirred tank reactor to provide agitation, the tip speed of the stirrer should be at least 60 centimeters per second, advantageously at least 75 centimeters per second with at least 85 centimeters per second providing especially good results.

Concentrations of the starting aqueous sulfide/hydrosulfide can vary from 1 weight percent up to saturation which can be as high as 60 weight percent or more, based upon the total weight of the aqueous solution. Specific embodiments of concentrations include from 10 to 40 weight percent and from 15 to 25 weight percent, with the understanding that the remaining weight percent is the amount of water in the aqueous sulfide/hydrosulfide. In one embodiment the amount of aqueous sulfide/hydrosulfide in the continuous reaction medium is from 56 to 94 weight percent, more specifically from 68 to 84 weight percent. The amount of carboxylic acid chloride/acid anhydride is from 16 to 31 weight percent, more specifically from 21 to 26 weight percent based on the total weight of the continuous reaction medium.

The continuous reaction is usually complete when the provision of carboxylic acid halide/acid anhydride which has been decided to be provided for whatever length of time in the continuous reaction is run has dissolved in the aqueous phase, an exotherm is no longer evident from this reaction and the evolution of any of the provided hydrogen sulfide subsides. As previously stated, one or more additional salts may optionally be present or be added to the aqueous thiocarboxylate salt product stream to increase its ionic strength when used in the subsequent thiocarboxylate silane-forming reaction. At the completion of the continuous thiocarboxylate salt-forming reaction, the product solution may optionally be continuously filtered to remove any particulate impurities and/or crystallized coproduced salts that may be present.

In one embodiment, the continuous process of making aqueous solution of the thiocarboxylate salt(s) may optionally be conducted such that the catalyst(s) is continuously recycled to the continuous process, such as in one example, by continuously filtering the catalyst using known means and then optionally continuously washing the catalyst with water and then continuously recycling the catalyst to fresh reactants.

EXAMPLES

The structure of the solid catalysts employed in the Examples is described below.

1st Step—Preparation of Aqueous Sodium Thiooctanoate

Sodium thiooctoanoate aqueous solution (STO) produced a batch production method was used in Examples 1-5, while Sodium thiooctoanoate aqueous solution from a continuous process was employed in Examples 6-7. The reagent molar ratio was the same in both the methods.

As far as the 2nd step is concerned, all these experiments were run with the continuous process. Thus Examples 1-5 are merely comparative as regards the first step which is conducted in a batch method, but the second step, i.e., the formation of the thiocarboxylate silane is within the invention herein in that it is conducted in a continuous manner. The reaction temperature, the flow rate and the catalyst amount were kept almost constant. The reagent molar ratio and the number of passes were varied, instead.

All the experimental details are summarized in the following series of tables.

The parameters reported are the reagent purity, amount and molar ratio, the reaction temperature, and the average flow rate. In addition, the average contact time ($\tau$, min) and the average space velocity ($\sigma$, grams reactants/(gram catalyst × min) per single pass) are listed.

Comparative Examples A and B are relative to continuous octanethioic acid S-[3-(triethoxy-silanyl)-propyl]ester process performed without catalyst, a control trial, and to the current inventive production conditions, respectively, and thus, are merely comparative as regards their absence of catalyst, not towards the method employed, which is within the methods of the invention.

Sodium thiooctanoate is prepared by reaction NaSH aqueous solution together with octanoyl chloride. The reaction is exothermic and generates $H_2S$. Its evolvement is made smoother by the presence of tetrabutyl ammonium bromide catalyst of the structure:

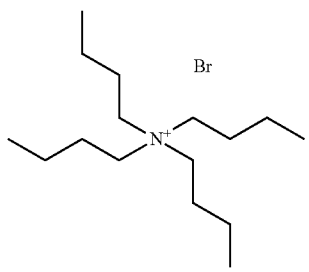 [SMILES: CCCC[N+](CCCC)(CCCC)CCCC ; Br]

Batch Procedure

In the example portions that employed the batch procedure, the reactor, equipped with a mechanical stirrer, a condenser, a caustic scrubber and kept under $N_2$ flow, was charged with a 24% by weight NaSH aqueous solution and tetrabutyl ammonium bromide catalyst. The mixture was strongly stirred and octanoyl chloride was slowly added to the mixture drop wise. The reaction temperature was kept below 32° C. The sodium thiooctanoate solution preparation was completed at the end of the octanoyl addition.

Continuous Procedure

The following procedure is meant to simulate the continuous stirred tank reactor operations. The tetrabutyl ammonium bromide catalyst was added to NaSH. NaSH and octanoyl chloride were fed to the reactor with two syringe pumps (see the below FIG. 1). The flask was initially empty and its bottom valve closed. The NaSH/octanoyl chloride was stirred at 400 RPM with a mechanical stirrer. The reaction started immediately and the $H_2S$ was neutralized in a caustic scrubber. The sodium thiooctanoate reaction is exothermic, therefore the flask was cooled with acetone and $N_2$ trying to avoid temperature above 32° C.

When the reaction flask was filled with desired amount of solution, the bottom valve was opened in order to collect continuously the sodium thiooctanoate in the receiver, while the NaSH and octanoyl chloride feeding was proceeding.

The process was stopped when the desired amount of material (about 200 grams) was collected in the receiver.

To verify the success of continuous stirred tank reactor production, the sodium thiooctanoate solutions were tested in the octanethioic acid S-[3-(triethoxy-silanyl)-propyl]ester (commonly referred to as 3-octanoylthio-1-propyltriethoxy silane) synthesis, according to the method described below.

2nd Step—Preparation of 3-octanoylthio-1-propyltriethoxysilane

The octanethioic acid S-[3-(triethoxy-silanyl)-propyl]ester (commonly referred to as 3-octanoylthio-1-propyltriethoxy silane) synthesis is performed through reaction between the sodium thiooctanoate and 3-chloropropyltriethoxy silane (CPTES).

Batch Procedure

The sodium thiooctanoate prepared according to the batch method from the 1st step was used in the 3-octanoylthio-1-propyltriethoxysilane synthesis process. The reactor was equipped with a mechanical stirrer, an external heating, a condenser and kept under an inert atmosphere. The sodium thiooctanoate solution was charged in the reactor, tetrabutyl ammonium bromide (TBAB) catalyst was added, then the mixture was heated to the desired temperature and vigorously stirred. When the reaction temperature was reached, the 3-chloropropyltriethoxysilane was added. The mixture was then kept at the target temperature under stirring for the time necessary to get the desired composition.

The two phase system was allowed to separate, and then the aqueous phase was removed, while the organic phase was purified by stripping the material at 70° C. and 50 mmHg vacuum. At the end of the process, typically 40% by weight of the initial mixture was organic phase and the remaining 60% by weight was brine. The resulting product purity was typically about 85-90% 3-octanoylthio-1-propyltriethoxysilane.

Continuous Procedure

Figure 3:
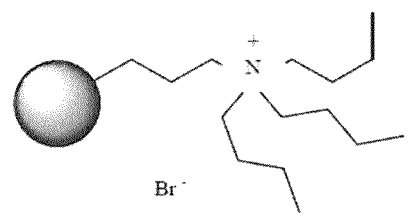
FIG. 3 is the chemical structure of bromide, tributylammonium propyl silica.

For the continuous octanethioic acid S-[3-(triethoxy-silanyl)-propyl]ester (commonly referred to as 3-octanoylthio-1-propyltriethoxysilane) production, a jacketed fixed bed reactor was used. The stainless steel tubular reactor was filled with solid catalyst. The reactor dimensions are inner diameter of 2.5 centimeters and a length of 25 centimeters and it was typically filled with 65-70 grams of catalyst. The catalyst employed was silica containing tributylpropyl ammonium bromide functional group, referred to as BAP7, whose structure is shown in FIG. 3.

The sphere represents the silica core supporting the functional group. The functionalities are quaternary ammonium salts, where the N-butyl groups are chemically bound to the silica through a propyl spacer and the anion is bromide. The functional group loading, pore size and particle size are listed in Table 1 below.

The amino functional groups account for the 16.4% by weight of the catalyst particles, while the rest is amorphous silica and propyl chains. This implies that the amount of catalyst that contains 1 mmol of BAP7 functionalities can be calculated as follows: (307.1/1000)×100/16.4=1.87 g.

TABLE 1

BAP7 physical properties.

| Particle size (μm) | Pore (Å) | N-butyl loading (mmol/g) | N-butyl loading % w/w | Molar weight g/mol |
|---|---|---|---|---|
| 200-500 | 80-110 | 0.535 | 16.4 | 307.1 |

Figure 4:
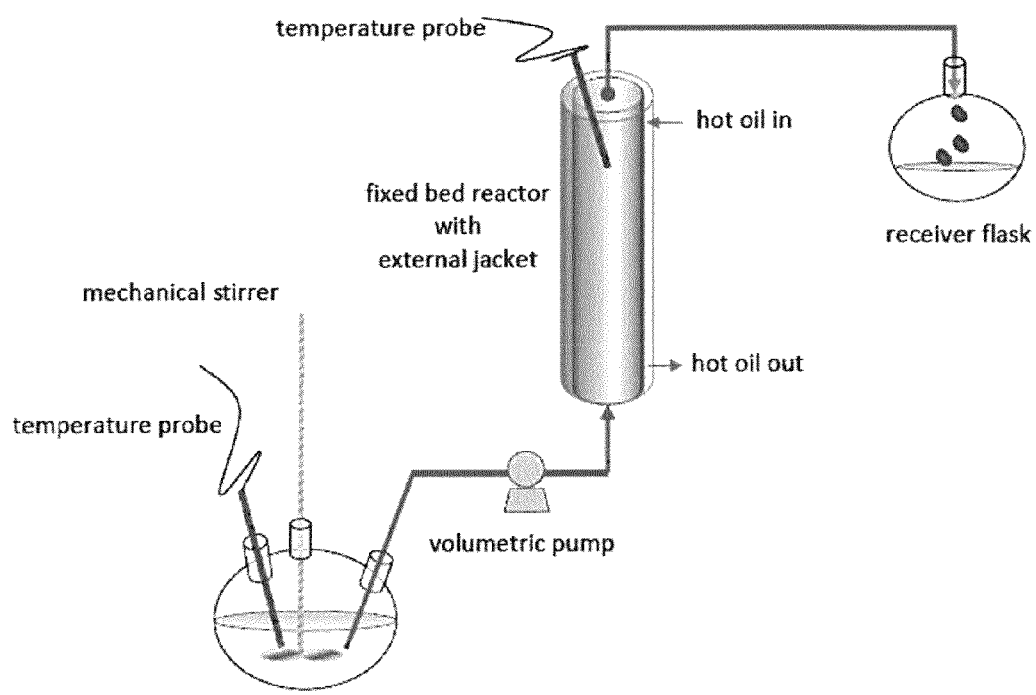
FIG. 4 is a drawing of a scheme of the fixed bed apparatus for the 3-octanoylthio-1 propyltriethoxysilane continuous production.

The experimental apparatus employed is depicted in FIG. 4 below.

A 1 liter 3-neck round bottom flask was charged with aqueous solution of sodium thiooctanoate and 3-chloropropyltriethoxysilane. The mixture was then vigorously stirred at 500-600 RPM and eventually heated. In the meanwhile, the fixed bed reactor was heated to reach the target temperature of 95° C. inside the column. The sodium thiooctanoate and 3-chloropropyltriethoxysilane mixture was then pumped to the fixed bed reactor. The aqueous/organic mixture coming out from the column was then collected in a receiver flask. The organic layer was sampled for analyses after each pass. The aqueous/organic mixture collected was then transferred back to the 3-neck flask to start a new pass.

The number of passes was from 5 to 7. At the end of the process, 40% by weight of the mixture was organic phase and the remaining 60% by weight was brine. The final product purity in the organic phase was typically in the range 70-85%. In a couple of experiments, a purification step was also performed. The aqueous phase was removed, while the organic phase was stripped at 70° C. and 50 mmHg vacuum, to remove moisture and ethanol.

Example 1

Aqueous solution of sodium thiooctanoate batch production, continuous 3-octanoylthio-1-propyltriethoxy silane production with stoichiometric ratio, 7 passes.

1$^{st}$ step conditions: reaction temperature: 23 < T < 31° C., reaction time: 30 min.

| Material | purity % | amount g | mol | molar ratio |
|---|---|---|---|---|
| NaSH | 24.0 | 233.8 | 3.0 | 2.2 |
| TBAB | 100.0 | 0.29 | 0.0009 | 0.2% |
| OC | 100.0 | 73.8 | 0.45 | 1.0 |

2$^{nd}$ step conditions:

| | stoichiometry | | | | fixed bed parameters | | | |
|---|---|---|---|---|---|---|---|---|
| Material | purity % | amount g | mol | molar ratio | T °C. | flow g/min | σ l/min | τ min | pass # |
| STO | 28.0 | 1363 | 0.21 | 1.0 | 96.0 | 7.2 | 0.11 | 9.75 | 7 |
| CPTES | 98.5 | 51.8 | 0.21 | 1.0 | | | | | |
| BAP7 | 16.4 | 65.4 | 0.035 | 16.7% | | | | | |

TBAB = tetrabutyl ammonium bromide; OC = octanoyl chloride
GC results: 79.7% 3-octanoylthio-1-propyltriethoxy silane, <0.1% 3-chloropropyltriethoxysilane (CPTES), 13.7% heavies.

Example 2

STO batch production, 10% molar excess of CPTES in the 3-octanoylthio-1-propyltriethoxy silane continuous process.

1$^{st}$ step conditions: reaction temperature: 23 < T < 33° C., reaction time: 45 min.

| Material | purity % | amount g | mol | molar ratio |
|---|---|---|---|---|
| NaSH | 24.0 | 233.6 | 1.0 | 2.2 |
| TBAB | 100.0 | 0.28 | 0.0009 | 0.2% |
| OC | 100.0 | 73.6 | 0.45 | 1.0 |

2$^{nd}$ step conditions:

| | stoichiometry | | | | fixed bed parameters | | | |
|---|---|---|---|---|---|---|---|---|
| Material | purity % | amount g | mol | molar ratio | T °C. | flow g/min | σ l/min | τ min | pass # |
| STO | 28.0 | 146.1 | 0.22 | 1.0 | 98.0 | 7.5 | 0.11 | 9.48 | 7 |
| CPTES | 98.5 | 61.0 | 0.25 | 1.1 | | | | | |
| BAP7 | 16.4 | 67.0 | 0.036 | 15.9% | | | | | |

GC results: 83.9% 3-octanoylthio-1-propyltriethoxy silane, 3.2% CPTES, 5.4% heavies. BAP7 = bromide, tributylammonium propyl silica

Example 3

Sodium thiooctanoate aqueous solution batch production, 10% molar excess of sodium thiooctanoate in the 3-octanoylthio-1-propyltriethoxysilane continuous process.

| | 1st step conditions: reaction temperature: 23 < T < 31° C., reaction time: 30 min. | | | |
|---|---|---|---|---|
| Material | purity % | amount g | mol | molar ratio |
| NaSH | 24.0 | 234.8 | 1.0 | 2.2 |
| TBAB | 100.0 | 0.29 | 0.0009 | 0.2% |
| OC | 100.0 | 73.8 | 0.45 | 1.0 |

| | 2nd step conditions: | | | | | | | |
|---|---|---|---|---|---|---|---|---|
| | stoichiometry | | | | fixed bed parameters | | | |
| Material | purity % | amount g | mol | molar ratio | T ° C. | flow g/min | σ l/min | τ min | pass # |
| STO | 28.0 | 146.4 | 0.22 | 1.1 | 95.5 | 6.5 | 0.09 | 10.7 | 5 |
| CPTES | 98.5 | 50.3 | 0.21 | 1.0 | | | | | |
| BAP7 | 16.4 | 68.5 | 0.037 | 17.8% | | | | | |

GC results: 71.8% 3-octanoylthio-1-propyltriethoxy silane, <0.1% CPTES, 19.8% heavies.

Example 4

STO batch production, continuous 3-octanoylthio-1-propyltriethoxy silane with stoichiometric ratio, 5 passes, final stripping.

| | 1st step conditions: reaction temperature: 23 < T < 31° C., reaction time: 45 min. | | | |
|---|---|---|---|---|
| Material | purity % | amount g | mol | molar ratio |
| NaSH | 24.0 | 233.8 | 1.0 | 2.2 |
| TBAB | 100.0 | 0.29 | 0.0009 | 0.2% |
| OC | 100.0 | 73.8 | 0.45 | 1.0 |

| | 2nd step conditions: | | | | | | | |
|---|---|---|---|---|---|---|---|---|
| | stoichiometry | | | | fixed bed parameters | | | |
| Material | purity % | amount g | mol | molar ratio | T ° C. | flow g/min | σ l/min | τ min | pass # |
| STO | 28.0 | 137.6 | 0.21 | 1.0 | 96.1 | 7.5 | 0.11 | 9.82 | 5 |
| CPTES | 98.5 | 52.7 | 0.22 | 1.0 | | | | | |
| BAP7 | 16.4 | 68.2 | 0.036 | 17.2% | | | | | |

GC results: 83.2% 3-octanoylthio-1-propyltriethoxy silane, 5.2% CPTES, 4.8% heavies;
GC results: 84.4% 3-octanoylthio-1-propyltriethoxy silane, 4.9% CPTES. 6.4% heavies (stripped sample).

Example 5

Sodium thiooctanoate aqueous solution batch production, continuous 3-octanoylthio-1-propyltriethoxy silane with sodium thiooctanoate/3-chloropropyltriethoxysilane mixture preheated at 85° C., final stripping.

| | 1st step conditions: reaction temperature: 23 < T < 29° C., reaction time: 120 min. | | | |
|---|---|---|---|---|
| Material | purity % | amount g | mol | molar ratio |
| NaSH | 24.0 | 467.6 | 2.0 | 2.2 |
| TBAB | 100.0 | 0.58 | 0.0018 | 0.2% |
| OC | 100.0 | 147.3 | 0.9 | 1.0 |

-continued

| | 2nd step conditions: | | | | | | | | |
|---|---|---|---|---|---|---|---|---|---|
| | stoichiometry | | | | fixed bed parameters | | | | |
| Material | purity % | amount g | mol | molar ratio | T ° C. | flow g/min | σ l/min | τ min | pass # |
| STO | 28.0 | 140.0 | 0.22 | 1.0 | 97.8 | 8.4 | 0.13 | 8.45 | 5 |
| CPTES | 98.5 | 53.4 | 0.22 | 1.0 | | | | | |
| BAP7 | 16.4 | 67.2 | 0.036 | 16.7% | | | | | |

GC results: 83.4% 3-octanoylthio-1-propyltriethoxy silane, 4.7% CPTES, 6.3% heavies;
GC results: 85.7% 3-octanoylthio-1-propyltriethoxy silane, 4.4% CPTES, 5.7% heavies (stripped sample).

These examples involve the sodium thiooctanoate aqueous solution continuous production process, as described above for the continuous production of the first step. In both the cases, the reagent molar ratio was the same, i.e. a 10% molar excess of NaSH with respect to the stoichiometry. Only the feeding rate was changed; the feeding rate was doubled in Example 7.

Example 6

STO $1^{st}$ step-continuous method, low feeding rate.

| | $1^{st}$ step conditions: reaction temperature: 23 < T < 32° C. | | | | |
|---|---|---|---|---|---|
| Material | purity % | amount g | mol | molar ratio | flow g/min |
| NaSH | 24.0 | 316.3 | 1.35 | 2.2 | 4.6 |
| TBAB | 100.0 | 0.39 | 0.0012 | 0.2% | * |
| OC | 100.0 | 100.3 | 0.62 | 1.0 | 1.5 |

| | 2nd step conditions: | | | | | | | | |
|---|---|---|---|---|---|---|---|---|---|
| | stoichiometry | | | | fixed bed parameters | | | | |
| Material | purity % | amount g | mol | molar ratio | T ° C. | flow g/min | σ l/min | τ min | pass # |
| STO | 28.0 | 140.3 | 0.22 | 1.0 | 98.8 | 8.6 | 0.13 | 7.97 | 5 |
| CPTES | 98.5 | 52.6 | 0.22 | 1.0 | | | | | |
| BAP7 | 16.4 | 68.3 | 0.036 | 16.6% | | | | | |

*TBAB was dissolved in the NaSH solution.
GC results: 83.1% 3-octanoylthio-1-propyltriethoxy silane, 11.2% CPTES, 2.3% heavies.

Example 7

STO $1^{st}$-step continuous method, high feeding rate.

| | $1^{st}$ step conditions: reaction temperature: 23 < T < 32° C. | | | | |
|---|---|---|---|---|---|
| Material | purity % | amount g | mol | molar ratio | flow g/min |
| NaSH | 24.0 | 230 | 0.98 | 2.2 | 9.2 |
| TBAB | 100.0 | 0.29 | 0.0009 | 0.2% | |
| OC | 100.0 | 73.0 | 0.45 | 1.0 | 3.1 |

| | 2nd step conditions: | | | | | | | | |
|---|---|---|---|---|---|---|---|---|---|
| | stoichiometry | | | | fixed bed parameters | | | | |
| Material | purity % | amount g | mol | molar ratio | T ° C. | flow g/min | σ l/min | τ min | pass # |
| STO | 28.0 | 139.8 | 0.21 | 1.0 | 94.8 | 9.1 | 0.14 | 7.54 | 5 |
| CPTES | 98.5 | 52.9 | 0.22 | 1.0 | | | | | |
| BAP7 | 16.4 | 67.2 | 0.036 | 16.7% | | | | | |

*TBAB was dissolved in the NaSH solution.
GC results: 77.3% 3-octanoylthio-1-propyltriethoxy silane, 16.3% 3-chloropropyltriethoxysilane, 2.3% heavies.

Comparative Example A

The sodium thiooctanoate aqueous solution used in this experiment was prepared according to the batch procedure for the $1^{st}$ step. A control trial, i.e. a $2^{nd}$ step without catalyst was performed. The fixed bed reactor was filled with silica microspheres, an inert solid material.

| | | $1^{st}$ step conditions: reaction temperature: $23 < T < 29°$ C., reaction time: 50 min. | | | |
|---|---|---|---|---|---|
| Material | purity % | amount g | mol | | molar ratio |
| NaSH | 24.0 | 233.5 | 1.0 | | 2.2 |
| TBAB | 100.0 | 0.29 | 0.0009 | | 0.2% |
| OC | 100.0 | 73.9 | 0.45 | | 1.0 |

| | | $2^{nd}$ step conditions: | | | | | | |
|---|---|---|---|---|---|---|---|---|
| | | stoichiometry | | | fixed bed parameters | | | |
| Material | purity % | amount g | mol | molar ratio | T ° C. | flow g/min | σ l/min | τ min | pass # |
| STO | 28.0 | 140.6 | 0.22 | 1.0 | 89.6 | 7.5 | 0.04 | 31.8 | 1 |
| CPTES | 98.5 | 53.44 | 0.22 | 1.0 | | | | | |
| Silica | 100.0 | 192.2 | 3.2 | 14.5 | | | | | |

GC results: 4.7% 3-octanoylthio-1-propyltriethoxy silane, 94.1% CPTES, <1% heavies.

Comparative Example B

Both sodium thiooctanoate aqueous solution and 3-octanoylthio-1-propyltriethoxy silane were produced according to the current production procedures described in the batch procedure for the $1^{st}$ step and the batch procedure for the $2^{nd}$ step, respectively.

| | | $1^{st}$ step conditions: reaction temperature: $23 < T < 32°$ C., | | |
|---|---|---|---|---|
| Material | purity % | amount kg | kmol | molar ratio |
| NaSH | 23.0 | 9723.8 | 39.9 | 2.2 |
| TBAB | 50.0 | 15.9 | 0.025 | 0.14% |
| OC | 100 | 2951.5 | 18.1 | 1.0 |

| | | $2^{nd}$ step conditions: reaction temperature: 95° C., reaction time: 7 h. | | |
|---|---|---|---|---|
| Material | purity % | amount kg | mol | molar ratio |
| STO | 28.0 | 1480.3 | 2.22 | 1.0 |
| CPTES | 98.5 | 546.5 | 2.24 | 1.0 |
| TBAB | 50 | 9.8 | 0.018 | 0.8% |

GC results: 89.1% 3-octanoylthio-1-propyltriethoxy silane, 1.2% CPTES, 4.6% heavies.

The results of Examples 1 to 7 and comparative Examples A and B are presented in Table 2.

TABLE 2

| Data from EXAMPLES 1 to 7 and COMPARATIVE EXAMPLE_A and B | | | |
|---|---|---|---|
| Example # | 3-octanoylthio-1-propyltriethoxy silane % | CPTES % | Heavies % |
| 1 | 79.7 | <0.1 | 13.7 |
| 2 | 83.9 | 3.2 | 5.4 |
| 3 | 71.8 | <0.1 | 19.8 |
| 4 | 83.2 | 5.2 | 4.8 |
| 5 | 83.4 | 4.7 | 6.3 |
| 6 | 83.1 | 11.2 | 2.3 |
| 7 | 77.3 | 16.3 | 2.3 |
| A | 4.7 | 94.1 | <1 |
| B | 89.1 | 1.2 | 4.6 |

The above noted examples clearly demonstrate the use of the solid catalyst in a continuous process both in the $1^{st}$ and $2^{nd}$ step effectively produces 3-octanoylthio-1-propyltriethoxy silane in quantitative amounts with much smaller levels of heavies than the batch procedure. In addition, the continuous method avoids the inherent problems with a batch procedure.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A process for the continuous preparation of thiocarboxylate silane comprising
(i) continuously feeding into a continuous plug flow reactor containing a solid supported catalyst comprising a salt of a positively charged nitrogen-containing functional group, (a) an aqueous liquid phase solution of an ammonium or alkali metal salt of thiocarboxylic acid, and
(b) a non-aqueous liquid phase haloalkylalkoxysilane:
(ii) continuously contacting the aqueous liquid phase solution of the ammonium or alkali metal salt of thiocarboxylate acid (a) with the non-aqueous liquid phase haloalkylalkoxysilane (b)
(iii) continuously reacting the ammonium or alkali metal salt of thiocarboxylate acid with the haloalkylalkoxysilane to form a non-aqueous liquid phase thiocarboxylate silane and an aqueous liquid phase solution of the ammonium or alkali metal salt of the halide;
(iv) continuously removing from the plug flow reactor the non-aqueous liquid phase thiocarboxylate silane and the aqueous liquid phase solution of the ammonium or alkali metal salt of the halide formed in step (iii); and
(v) separating the non-aqueous liquid phase thiocarboxylate silane from the aqueous liquid phase solution of the ammonium or alkali metal salt of the halide formed in step (iv),
to provide a continuous stream of thiocarboxylate silane reaction product.

2. The process of claim 1 wherein the continuous plug flow reactor is a continuous tubular plug-flow fixed bed reactor.

3. The process of claim 2 wherein the continuous tubular plug-flow fixed bed reactor has a ratio of internal diameter to length of from 3 to 100.

4. The process of claim 2 wherein the continuous tubular plug-flow fixed bed reactor has an average contact time r in a single pass of from 5 to 40 minutes.

5. The process of claim 2 wherein the continuous tubular plug-flow fixed bed reactor has an average space velocity in a single pass 6 of from a 0.01 to about 0.20 minutes$^{-1}$.

6. The process of claim 1 further comprising continuously sending the continuous stream of thiocarboxylate silane reaction product to a continuous phase separator and continuously separating the continuous stream of thiocarboxylate silane reaction product into an organic phase containing thiocarboxylate silane product and an aqueous waste phase in the continuous phase separator.

7. The process of claim 6 wherein the continuous phase separator is a two-phase product decanter.

8. The process of claim 6 wherein the rate of the continuous sending of the continuous stream of thiocarboxylate silane reaction product from the continuous plug flow reactor to the continuous phase separator is such that the phase separation is continuous.

9. The process of claim 6 further comprising sending the separated organic phase to at least one separatory column and continuously removing byproducts and/or unreacted haloalkyl silane in the at least one separatory column.

10. The process of claim 9 wherein the at least one separatory column comprises at least two separatory columns in series wherein a first separatory column operating at a first temperature and a first vacuum removes at least one of alkanol, water and tetraalkylorthosilicate and a second separatory column operating at a second temperature and a second vacuum which are higher than the first temperature and first vacuum wherein the second separatory column removes unreacted haloalkyl silane.

11. The process of claim 9 wherein the rate of feed from the continuous phase separator to the at least one separatory column is such that the rate of removal of byproducts and/or unreacted haloalkylalkoxysilane in the at least one separatory column is continuous.

12. The process of claim 1 wherein the continuous stream of thiocarboxylate silane reaction product is recycled into the continuous plug flow reactor at least one time prior to being sent to the continuous phase separator.

13. The process of claim 12 wherein the continuous stream of thiocarboxylate silane reaction product is recycled into the continuous plug flow reactor from 5 to 10 times prior to being sent to the continuous phase separator.

14. The process of claim 1 wherein the aqueous solution of a salt of a thiocarboxylic acid and the haloalkylalkoxysilane are first continuously premixed in a premix reactor.

15. The process of claim 14 wherein the aqueous solution of a salt of a thiocarboxylic acid and the haloalkylalkoxysilane are continuously sent to the premix reactor from two separate vessels wherein one of the separate vessels contains and/or is continuously fed with the aqueous solution of a salt of a thiocarboxylic acid and the other of the two separate vessels contains and/or is continuously fed with the haloalkylalkoxysilane.

16. The process of claim 15 wherein the rate of the continuous feed of the aqueous solution of a salt of a thiocarboxylic acid and the rate of the continuous feed of the haloalkylalkoxysilane is such that it provides a continuous stream of reactants to the premix reactor and the rate of the feed of the premixed reactants in the premix reactor to the continuous plug flow reactor is such that the reaction of aqueous solution of a salt of a thiocarboxylic acid and haloalkylalkoxysilane in the continuous plug flow reactor is continuous.

17. The process of claim 1 wherein the solid supported catalyst comprising a salt of a positively charged nitrogen-containing functional group, wherein the positively charged nitrogen-containing functional group has the chemical Formula (1):

$$[-R^1N(R^2)_2-R^3]^+X^- \quad (1)$$

wherein
R$^1$ is a divalent alkylene, cycloalkylene, alkenylene, aralkylene, arylene, arenylene group having from 1 to 20 carbon atoms;
each R$^2$ is independently a monovalent alkyl, cycloalkyl, alkenyl, aralkyl, aryl or arenyl group having from 1 to 20 carbon atoms or hydrogen,
each R$^3$ is a monovalent alkyl, cycloalkyl, alkenyl, aralkyl, aryl or arenyl group having from 1 to 20 carbon atoms, hydrogen or —C(=NR$^2$)—NR$^2$ group;
X$^-$ is fluoride, chloride, bromide or iodide.

18. The process of claim 1 wherein the solid supported catalyst comprising a salt of a positively charged nitrogen-containing functional group has the chemical Formula (2):

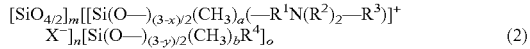

$$[SiO_{4/2}]_m[[Si(O-)_{(3-x)/2}(CH_3)_a(-R^1N(R^2)_2-R^3)]^+ X^-]_n[Si(O-)_{(3-y)/2}(CH_3)_bR^4]_o \quad (2)$$

wherein
R$^1$ is a divalent alkylene, cycloalkylene, alkenylene, aralkylene, arylene, arenylene group having from 1 to 20 carbon atoms;
each R$^2$ is independently a monovalent alkyl, cycloalkyl, alkenyl, aralkyl, aryl or arenyl group having from 1 to 20 carbon atoms or hydrogen,
each R$^3$ is a monovalent alkyl, cycloalkyl, alkenyl, aralkyl, aryl or arenyl group having from 1 to 20 carbon atoms, hydrogen or —C(=NR$^2$)—NR$^2$ group;
each R$^4$ is independently monovalent alkyl, cycloalkyl, arenyl, aryl or arenyl group containing from 1 to 18 carbon atoms, and optionally containing at least one oxygen, nitrogen or sulfur atom, —OH or —OR$^2$ group, and m is greater than 1; n is greater than 1; o is greater than 1; x is 0, 1 or 2; and y is 0, 1 or 2.

19. The process of claim 18 wherein m is 50 to 10,000; n is greater than 5 to 500; o is 0 to 500; x is 0, 1 or 2; y is 0, 1 or 2; R' is methylene, ethylene or propylene; $R^2$ is methyl, ethyl, n-propyl, isopropyl, n-butyl, isobutyl, n-pentyl or n-hexyl; $R^3$ is methyl, ethyl, n-propyl, isopropyl, n-butyl, isobutyl, n-pentyl, n-hexyl, —(C=N(CH$_3$)$_2$N(CH$_3$)$_2$) or —(C=N(CH$_2$CH$_3$)$_2$N(CH$_2$CH$_3$)$_2$); $R^4$ is methyl, ethyl, n-propyl, isopropyl, n-butyl, isobutyl, n-pentyl or n-hexyl, hydroxyl, methoxy, ethoxy, propoxy, isopropoxy, butoxy or pentoxy; and X is chloride or bromide.

20. The process of claim 18 wherein the solid supported catalyst comprising a salt of a positively charged nitrogen-containing functional group is selected from the group consisting of chloride, tributylammonium propyl, silica; chloride, tributylammonium propyl 2-hydroxyethylsulfide ethyl silica; chloride, tributylammonium propyl dodecylsulfide ethyl silica; bromide, tributylammonium propyl, silica; combinations thereof and aqueous solutions thereof.

21. The process of claim 1 wherein the thiocarboxylate silane is 3-octanoylthio-1-propyltriethoxy silane.

22. The process of claim 1 wherein the aqueous liquid phase solution of an ammonium or alkali metal salt of thiocarboxylic acid of step (i)(a) is prepared by continuously reacting in a continuous stirred tank reactor an aqueous solution of a sulfide and/or hydrosulfide with a carboxylic acid halide and/or acid anhydride to provide a continuous stream of aqueous solution of thiocarboxylic acid salt.

23. The process of claim 22 wherein the aqueous solution of a sulfide and/or hydrosulfide and the carboxylic acid halide and/or acid anhydride are continuously added at a fixed rate to the continuous stirred tank reactor and the continuous stream of aqueous solution of thiocarboxylic acid salt and H$_2$S are continuously removed from the continuous stirred tank reactor at a fixed rate wherein the rate of addition and removal are such that the reaction is continuous.

24. The process of claim 23 wherein the continuous stirred tank reactor is maintained at a temperature of from 20° C. to 35° C.

25. The process of claim 22 wherein prior to the commencement of the continuous reaction, the aqueous solution of a sulfide and/or hydrosulfide and the carboxylic acid halide and/or acid anhydride are provided to the continuous stirred tank reactor until the contents of the continuous stirred reactor occupy a desired volume of from 50 to 90 percent of the volume of the continuous stirred reactor.

26. The process of claim 22 wherein the continuous stirred tank reactor further contains a homogenous catalyst, tetrabutyl ammonium bromide.

27. The process of claim 1 wherein the continuous plug flow reactor is a continuous tubular plug-flow fixed bed reactor, having a ratio of internal diameter to length of from 3 to 100, an average contact time τ in a single pass of from 5 to 40 minutes and an average space velocity σ in a single pass of from 0.01 to 0.20 minutes.

28. The process of claim 1, wherein separating the non-aqueous liquid phase thiocarboxylate silane from the aqueous liquid phase solution of the ammonium or alkali metal salt of the halide formed in step (iv) is carried out in the two-phase product decanter.

29. The process of claim 1 further comprising sending the separated continuous stream of thiocarboxylate silane reaction product to at least two separatory columns in series wherein a first separatory column operating at a first temperature and a first vacuum removes at least one of alkanol, water and tetraalkylorthosilicate and a second separatory column operating at a second temperature and a second vacuum which are higher than the first temperature and first vacuum wherein the second separatory column removes unreacted haloalkylalkoxysilane.

30. The process of claim 1 wherein the solid supported catalyst comprising a positively charged nitrogen-containing functional group is selected from the group consisting of chloride, tributylammonium propyl, silica; chloride, tributylammonium propyl 2-hydroxyethylsulfide ethyl silica; chloride, tributylammonium propyl dodecylsulfide ethyl silica; bromide, tributylammonium propyl, silica; combinations thereof and aqueous solutions thereof.

* * * * *